United States Patent
Zhou et al.

(10) Patent No.: US 11,034,651 B2
(45) Date of Patent: Jun. 15, 2021

(54) LIGHT COLORED MODIFIED ISOCYANATE MIXTURE AND PREPARATION METHOD THEREOF

(71) Applicant: Wanhua Chemical Group Co., Ltd., Shandong (CN)

(72) Inventors: Ye Zhou, Shandong (CN); Wenbo Wang, Shandong (CN); Yilu Xia, Shandong (CN); Hongke Zhang, Shandong (CN); Xiaogao Liu, Shandong (CN); Guiying Niu, Shandong (CN); Huihui Wang, Shandong (CN); Xueting Liu, Shandong (CN)

(73) Assignee: Wanhua Chemical Group Co., Ltd.

( * ) Notice: Subject to any disclaimer, the term of this patent is extended or adjusted under 35 U.S.C. 154(b) by 0 days.

(21) Appl. No.: 16/645,612

(22) PCT Filed: Aug. 2, 2018

(86) PCT No.: PCT/CN2018/098253
§ 371 (c)(1),
(2) Date: Mar. 9, 2020

(87) PCT Pub. No.: WO2019/076099
PCT Pub. Date: Apr. 25, 2019

(65) Prior Publication Data
US 2020/0283375 A1    Sep. 10, 2020

(30) Foreign Application Priority Data
Oct. 20, 2017   (CN) .......................... 201710981296.3

(51) Int. Cl.
*C07C 265/14*   (2006.01)
*C07C 267/00*   (2006.01)
*C07C 263/18*   (2006.01)

(52) U.S. Cl.
CPC .......... *C07C 265/14* (2013.01); *C07C 263/18* (2013.01); *C07C 267/00* (2013.01)

(58) Field of Classification Search
CPC ... C07C 263/18; C07C 265/14; C07C 267/00; C07D 229/00
See application file for complete search history.

(56) References Cited

U.S. PATENT DOCUMENTS

| | | | |
|---|---|---|---|
| 2,663,737 A | 12/1953 | McCormack et al. | |
| 2,853,473 A | 9/1958 | Campbell et al. | |
| 4,088,665 A | 5/1978 | Findeisen et al. | |
| 4,120,884 A | 10/1978 | Woerner et al. | |
| 5,202,358 A | 4/1993 | Scholl et al. | |
| 6,120,699 A | 9/2000 | Narayan et al. | |
| 2004/0106789 A1 | 6/2004 | Richter et al. | |
| 2005/0282993 A1 | 12/2005 | Rosthauser et al. | |
| 2006/0025557 A1 | 2/2006 | Wershofen et al. | |
| 2007/0155937 A1 | 7/2007 | Wershofen et al. | |
| 2007/0167633 A1 | 7/2007 | Wershofen et al. | |
| 2010/0120992 A1 | 5/2010 | Kamiyama et al. | |
| 2013/0012698 A1 | 1/2013 | Bosman et al. | |
| 2017/0253688 A1* | 9/2017 | Yamauchi | C08G 18/02 |

FOREIGN PATENT DOCUMENTS

| | | | |
|---|---|---|---|
| CN | 1502605 A | | 6/2004 |
| CN | 1721395 A | | 1/2006 |
| CN | 1789241 A | | 6/2006 |
| CN | 101003496 A | | 7/2007 |
| CN | 101553517 A | | 10/2009 |
| CN | 102718683 | * | 10/2012 |
| CN | 102718683 A | | 10/2012 |
| CN | 102858747 A | | 1/2013 |
| CN | 102964566 A | | 3/2013 |
| CN | 107879951 A | | 4/2018 |
| EP | 515933 A2 | | 12/1992 |
| JP | S54100345 A | | 8/1979 |
| JP | 2008143799 A | | 6/2008 |
| JP | 2009522317 A | | 6/2009 |
| WO | 2007006622 A1 | | 1/2007 |
| WO | 2007076998 A1 | | 7/2007 |
| WO | 2008009669 A1 | | 1/2008 |

OTHER PUBLICATIONS

CN 102718683 translated (Year: 2012).*
International Search Report for PCT/CN2018/098253 dated Nov. 7, 2018.

* cited by examiner

*Primary Examiner* — Yevgeny Valenrod
*Assistant Examiner* — Blaine G Doletski
(74) *Attorney, Agent, or Firm* — Lerner, David, Littenberg, Krumholz & Mentlik, LLP

(57) ABSTRACT

Disclosed is a light colored modified isocyanate mixture and a preparation method thereof. The method comprises the following steps: a) reacting isocyanate groups of a raw material isocyanate under the action of a phospholenecatalyst, and finally obtaining a modified isocyanate reaction solution containing carbodiimide and/or uretonimine derivatives; and b) adding a compounded terminator of a halosilane organic and a sulfonic anhydride to the reaction solution obtained in step a so as to terminate the reaction of carbodiimidization. The modified isocyanate prepared by the method has the characteristics of a liquid state at room temperature, being stable in storage at room temperature and high temperature, and low color number.

20 Claims, No Drawings

LIGHT COLORED MODIFIED ISOCYANATE MIXTURE AND PREPARATION METHOD THEREOF

CROSS REFERENCE TO RELATED APPLICATIONS

The present application is a national phase entry under 35 U.S.C. § 371 of International Application No. PCT/CN2018/098253, filed Aug. 2, 2018, which claims priority from Chinese Patent Application No. 201710981296.3 filed Oct. 20, 2017, all of which are hereby incorporated herein by reference.

TECHNICAL FIELD

The invention relates to a light colored modified isocyanate mixture and preparation method thereof, the modified isocyanate mixture contains carbodiimide (CDI) and/or uretonimine (UTI) derivatives, which is liquid at normal temperature and with low-color number, and has good stability at normal temperature storage and at high temperature.

TECHNICAL BACKGROUND

Isocyanates can form carbodiimide derivatives after releasing $CO_2$ by polycondensation under certain conditions, the carbodiimide group can be adducted with the isocyanate to form the uretonimine group. By this method, the isocyanate is allowed to contain CDI and UTI substances, which can reduce the melting point of the isocyanate, make it liquid at normal temperature, and form a stable low-viscosity liquid that is easy to transport and has good storage stability. And the products prepared from such modified isocyanate have been improved in the properties such as light resistance, flame resistance, hydrolysis resistance, and increased initial strength and the like to a certain degree.

High-efficiency catalyst of phospholene, especially high-efficiency catalyst of phospholene oxide can be simply used for isocyanate group. Under certain reaction conditions, the isocyanate is heated and partially converted into carbodiimide and/or uretonimine derivatives, and the preparation method can refer to the methods in U.S. Pat. Nos. 6,120,699, 2,853,473 and EP-A-515933.

Phospholene catalyst, especially phospholene oxide catalyst, is expected to have high activity, in order to be able to activate the carbodiimidation under mild temperature conditions, but the catalyst still has sufficient activity at room temperature to affect the storage stability of products containing free NCO groups, and during the process, the NCO groups are continuously consumed which makes the viscosity continuously increase, thus the catalyst needs to be deactivated by chemical or physical or other methods.

In order to terminate the reaction of forming NCO to continuously produce CDI groups and UTI groups, a limited amount of terminator can be added to the reaction solution, thereby deactivating the high-efficiency catalyst. Suitable terminators are mentioned in patent specifications EP-A-515933, CN-A-1721395, U.S. Pat. No. 4,120,884, CN-A-1789241, and CN-A-102718683, including Lewis acids, acyl chlorides, chloroformic acids, aromatic sulfonic acids/esters, silylated acids, alkyl sulfates and halides of main group elements. Terminating the catalysis with acids is not effective enough, in which the acid can also exist in the form of acyl chloride.

With reference to the publication of patent specification EP-A-515933, for the isocyanate mixture containing CDI/UTI groups prepared by phospholene catalyst, the activity of the catalyst is terminated by using at least the equimolar amount of, preferably 1-2 times molar amount of such as trimethylsilyl trifluoromethanesulfonate (TMST) as the catalyst. However, it has been proved in practice that the modified isocyanate prepared by this method has problems such as incomplete termination and poor storage stability, especially in the environment where the outdoor temperature is relatively low in winter, the product needs to be water bathed to melt in the process of using, and during the process of melting, gas will be generated, which will lead to high pressure in the storage vessel, and NCO of the product will decrease significantly and the viscosity will increase significantly.

With reference to the publication of patent specification CN-A-1721395, the silylated acid such as trimethylsilyl trifluoromethanesulfonate is used to terminate the activity of catalyst, the intended purpose can be achieved by the amount of terminator, but the appearance color number of the product rises rapidly. By compounding trimethylsilyl trifluoromethanesulfonate with non-silylated acid, acyl chloride and sulfonate, the patent improves the termination effect of the terminator, improves the stability of the product, and the color number of the product can reach to 50-60APHA, however in the current technical field, the appearance color still cannot meet our needs, and the viscosity of the product increases significantly during the high temperature heating process.

With reference to the publication of the patent specification U.S. Pat. No. 4,120,884, dimethyl sulfate is used to terminate the phospholene oxide catalyst, and the storage stability has a certain improvement compared to using TMST, but the viscosity during the process of melting the material increases significantly.

According to the specification of CN-A-1789241, the alkylation reagents such as trifluoromethanesulfonates are used to terminate the reaction, the stability can be achieved by increasing the molar equivalent ratio of the terminator and the catalyst to achieve complete termination, but the color number of the product is not ideal.

CN-A-102718683 optimizes this, acid anhydride terminator is used to terminate the phospholene or phospholene oxide catalyst, and the preferred terminator is trifluoromethylsulfonic anhydride and/or p-toluenesulfonic anhydride. It has been proved in practice that the storage stability at room temperature has been improved to a certain extent, but the high temperature stability is not ideal, the NCO has decreased significantly, and the color number of the product has increased rapidly, the trifluoromethylsulfonic anhydride and/or p-toluenesulfonic anhydride terminators are now the most effective terminators in the prior art.

The existing methods for preparing liquid isocyanates containing CDI and/or UTI groups are difficult to overcome the above drawbacks.

SUMMARY OF THE INVENTION

The invention relates to a light colored modified isocyanate mixture and preparation method thereof, the modified isocyanate mixture contains carbodiimide (CDI) and/or uretonimine (UTI) derivatives, which is liquid at normal temperature and with low-color number and has good normal temperature storage and high temperature stability.

The present invention has found in research that halosilane organics and sulfonic anhydride substances do not contain —OH or active hydrogen atoms, thus have better termination effects, which are better than that of acid substances, alkylating agents and single anhydride terminators, and the modified isocyanate prepared containing CDI and/or UTI groups has good stability, and the viscosity will not increase even during high temperature degradation.

The specific technical solutions are as follows:

A method for preparing a light colored modified isocyanate mixture, the modified isocyanate mixture contains carbodiimide (CDI) and/or uretonimine (UTI) derivatives, and the method includes the following steps:

a) subjecting the isocyanate group of a raw material isocyanate to carbodiimidization under the action of a phospholene catalyst to obtain a reaction solution of modified isocyanate containing carbodiimide and/or uretonimine derivatives;

b) adding a compounded terminator to the reaction solution obtained in step a) to terminate the carbodiimidization;

the terminator is a compound of a halosilane organic and a sulfonic anhydride substance.

The reaction of step a) can be carried out at a temperature of 40° C.-210° C., preferably 100° C.-200° C., more preferably 150° C.-200° C., and further preferably 190-200° C.

Furthermore, the halosilane organic has a chemical formula of the following formula (I),

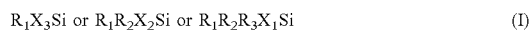

$R_1X_3Si$ or $R_1R_2X_2Si$ or $R_1R_2R_3X_1Si$ (I)

in the molecular formula (I), $R_1$, $R_2$ and $R_3$ independently represent an aliphatic, aromatic, araliphatic, and cycloaliphatic group optionally containing heteroatoms, wherein "optionally" means that it may contain or not contain heteroatoms. In the molecular formula (I), $R_1$, $R_2$ and $R_3$ independently represent aliphatic (such as, C1-C10 hydrocarbyl, preferably C1-C6 hydrocarbyl, for example methyl, ethyl, n-propyl, isopropyl, n-butyl, isobutyl, t-butyl, etc.), aromatic (such as C6-C15 aromatic groups, specifically for example, phenyl, tolyl, ethylphenyl, etc.), araliphatic (such as C7-C15 araliphatic groups, specifically for example, phenmethyl, phenethyl, etc.), cycloaliphatic (such as C3-C12 cycloaliphatic groups, specifically for example, cyclopropyl, cyclobutyl, cyclohexyl, cyclopentyl, etc.) and other groups, which may contain heteroatoms and/or other functional groups, wherein $R_1$, $R_2$ and $R_3$ may be the same or different; two of $R_1$, $R_2$ and $R_3$ may be connected to each other to form a ring structure, that is, for $R_1R_2X_2Si$, $R_1$ and $R_2$ may be connected to each other to form a ring structure or not to form a ring structure; for $R_1R_2R_3X_1Si$, any two groups of $R_1$, $R_2$ and $R_3$ may be connected to each other to form a ring structure or not to form a ring structure; X represents the halogen element and may be represented as fluorine, chlorine and bromine and other elements. Specifically, the subscript numbers 1, 2, and 3 in $X_1$, $X_2$, and $X_3$ all refer to the number of X in the molecular formula; for $R_1X_3Si$ or $R_1R_2X_2Si$, in which two or three of X may be the same or different; and the subscript number of R groups such as $R_1$, $R_2$ and $R_3$ are only for the convenience of distinguishing each R group, not the meaning of number, and the meanings of other similarities in the invention are the same. The halosilane organic is preferably one or two or more of diphenyldifluorosilane, diphenyldichlorosilane, tritylfluorosilane, and tert-butyltrichlorosilane.

Further, the said sulfonic anhydride substance has the following structural formula (II):

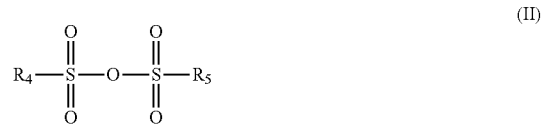

in the structural formula (II), $R_4$ and $R_5$ independently represent an aliphatic, aromatic, araliphatic, and cycloaliphatic and the other groups optionally containing heteroatoms and/or other functional groups, wherein "optionally" means that it may contain or not contain heteroatoms and/or other functional groups. Furthermore, $R_4$ and $R_5$ independently represent aliphatic (such as C1-C10 hydrocarbyl, preferably C1-C6 hydrocarbyl, for example methyl, ethyl, n-propyl, isopropyl, n-butyl, isobutyl, t-butyl, etc.), aromatic (such as C6-C15 aromatic groups, specifically for example, phenyl, tolyl, ethylphenyl, etc.), araliphatic (such as C7-C15 araliphatic groups, specifically for example, phenmethyl, phenethyl, etc.), cycloaliphatic (such as C3-C12 cycloaliphatic groups, specifically for example, cyclopropyl, cyclobutyl, cyclohexyl, cyclopentyl, etc.) and other groups, which may contain heteroatoms and/or other functional groups, wherein $R_4$ and $R_5$ may be the same or different, the two groups $R_4$ and $R_5$ may optionally be connected to each other to form a ring structure, wherein "optionally" means that they may be connected to each other to form a ring structure or not to form a ring structure. The said sulfonic anhydride substance is preferably one or two or more of p-toluenesulfonic anhydride, methanesulfonic anhydride, ethylsulfonic anhydride, and trifluoromethanesulfonic anhydride.

The preferred terminator is a compound of diphenyldifluorosilane and p-toluenesulfonic anhydride.

The amount of compounded terminator is based on the weight of raw material isocyanate, the amount of organosilane terminator (halosilane organic terminator) is 50-2000 ppm, preferably 100-600 ppm, most preferably 100-200 ppm; the amount of sulfonic anhydride terminator is 10-200 ppm, preferably 10-100 ppm, and most preferably 10-50 ppm. The compounding ratio (mass ratio) of the halosilane terminator to the sulfonic anhydride is preferably 2-6:1, further preferably 3-5:1, and more preferably 4:1.

The catalyst used for preparing the isocyanate containing carbodiimide and/or uretonimine derivatives is a phospholene catalyst and/or a phospholeneoxide, the phospholene or phospholene oxide catalyst is preferred. The catalysts are known, such as described both in EP-A-515933 and U.S. Pat. No. 2,663,737, and the typical examples of these catalysts are known in the art.

Preferred catalyst is 1-methyl-3-methyl-3-phospholene-1-oxide or 1-phenyl-3-methyl-3-phospholene. The polycondensation of isocyanate is performed in the presence of the above-mentioned catalyst, and the amount of the catalyst is 0.1-10 ppm, preferably 0.2-2 ppm, and the preferred amount is 0.5 ppm, relative to the weight of the raw material isocyanate.

Any suitable isocyanate can be used as the raw material isocyanate in the method of the present invention. However, in the method of the present invention, diisocyanate is preferred, such as one or more selected from the group consisting of aromatic, araliphatic, aliphatic, and cycloaliphatic diisocyanates, and it is particularly preferred that the diphenylmethane diisocyanate is subjected to carbodiimidation.

In some embodiments, the raw material isocyanate is diphenylmethane diisocyanate, wherein the diphenylmethane diisocyanate contains 97-100 wt % 4,4-isomer, 0-1 wt % 2,2-isomer, and 0.5-1.8 wt % 2,4-isomer.

The carbodiimidation is carried out in the presence of a high-efficiency catalyst, and the reaction is carried out at a temperature of 40-210° C., preferably between 190° C.-200° C., of course, the reaction can also be carried out at a mild ambient temperature, but this requires a large amount of catalyst, and the large additive amount of terminator will lead to the color number of the product to be unsatisfactory; a small amount of catalyst will cause a slow reaction rate, which is not conducive to industrial production.

Because the carbodiimidation is an NCO polycondensation and the process is accompanied by the generation of $CO_2$, such reaction process can be monitored by measuring the amount of $CO_2$ released; or the change in the refractive index of the reaction solution can be continuously determined to reflect the changes in NCO content. When the carbodiimidation time reaches 10 min-24 h, preferably between 1 h-4 h, a compounded terminator is added to terminate the reaction.

In some specific embodiments, the temperature condition of adding a compounded terminator to terminate the carbodiimidation of step b) is 40-70° C., further preferably 40-60° C., more preferably 50-60° C., such as 60° C.

According to some embodiments of the present invention, 5-20% of, preferably 10-15% of the NCO group of the raw material isocyanate is converted into CDI group by carbodiimidation, and then the CDI group reacts with the unreacted NCO group to form UTI group, so that the UTI group is easily introduced into the isocyanate system. Since the conversion of CDI group to UTI group is a reversible process, a small amount of CDI groups will remain in the product.

After the reaction of step a) and before adding the terminator, an appropriate amount of the raw material isocyanate can be further added, of course, this step can also be performed without the further adding operation, further adding the isocyanate raw material mainly can accelerate the cooling process; after adding the terminator, an appropriate amount of the raw material isocyanate can be further added again, or not be further added again, further adding isocyanate after adding the terminator is mainly for adjusting the target NCO value; the total amount of the further added isocyanate raw material is determined according to the NCO value to be adjusted as needed.

The positive effects of the present invention are as follows: a) the modified isocyanate product obtained by the present invention has excellent storage stability at normal temperature, and will not undergo polycondensation during the process of melting at high-temperature, the content of NCO group does not decrease even at high temperatures in the storage of the product, and the viscosity change is very small; b) the modified isocyanate prepared by the present invention has a lower color number, which is generally stable at 20-30 APHA, and the color number is significantly reduced compared with the prior art.

The invention further relates to a liquid modified isocyanate mixture containing CDI and/or UTI groups obtained by the above method, the NCO content is 20-32 wt %, preferably 28-30 wt %; the viscosity is 10-200 cp, preferably 20-60 cp, the color number is 20-40 APHA; preferably, the initial value of the product ⓢ Hasen color number is 20-30, and the value after 2 months is 25-35. The advantages of the method according to the present invention are obvious, since a compound of halosilane organic and sulfonic anhydride terminator is used, the isocyanate containing CDI and/or UTI groups is basically light-colored and has storage stability at normal temperature and high temperature. These and other advantages and benefits of the invention will be apparent from the following specific embodiment of the invention.

EMBODIMENTS

The present invention is further illustrated by the following examples, but the scope of the present invention is not limited to the following examples.

The raw material: diphenylmethane diisocyanate, wherein the diphenylmethane diisocyanate contains 97-100 wt % 4,4-isomer, 0-1 wt % 2,2-isomer, and 0.5-1.8 wt % 2,4-isomer, the content of NCO is 33.6 wt %.

The catalyst is: a solution of 1-methyl-3-methyl-3-phospholene-1-oxide or 1-phenyl-3-methyl-3-phospholene-1-oxide, using dichloromethane as the solvent, and the concentration of catalyst was 1% relative to the mass of the solvent dichloromethane; both the catalyst and the solvent were purchased and available from Sinopharm.

Diphenyldifluorosilane, purity 96%, color number 10 #, from Suzhou Yake Technology Co., Ltd.

Tritylfluorosilane, purity 96%, available from Sinopharm.

P-toluenesulfonic anhydride, purity 95%, available from Sinopharm.

Trifluoromethanesulfonic anhydride, purity 98%, available from Sinopharm.

Trimethylsilyltrifluoromethanesulfonate, purity 95%, available from Sinopharm.

Dibutyl phosphate, purity 98%, available from Sinopharm.

Comparative Example 1

500 g diphenylmethane diisocyanate was heated to about 50° C. under the protection of $N_2$ while stirring, and a high-efficiency catalyst solution of phospholene (i.e., a solution of 1-phenyl-3-methyl-3-phospholene-1-oxide) with a catalyst amount of 0.5 ppm (0.025 g) was added, after mixing, the mixture was quickly heated to 200° C., and after reacting for 90 minutes, 200 g diphenylmethane diisocyanate was further added, and 200 ppm (0.1 g) of terminator diphenyldifluorosilane was added, the temperature was rapidly reduced to 60° C., after stirring the mixture for 30 minutes, 200 g diphenylmethane diisocyanate was further added again, then the temperature was raised to 70-80° C., and stirred for 120 min to obtain the final product. The test results of the final product are shown in tables 1-2.

This comparative example can also be carried out according to the following steps: 500 g diphenylmethane diisocyanate was heated to about 50° C. while stirring under the protection of $N_2$, and a high-efficiency catalyst solution of 1-phenyl-3-methyl-3-phospholene with a catalyst amount of 0.025 g was added, after mixing the mixture was quickly heated to 200° C., and 400 g diphenylmethane diisocyanate was further added after reacting for 90 minutes, and after the temperature was rapidly cooled to 60° C., 0.1 g terminator diphenyldifluorosilane was added, and the mixture was stirred for 30 minutes and then heated to 70-80° C., and stirred for 120 minutes to obtain the final product. There is no significant change in the properties of this product relative to the properties of the product prepared according to the aforementioned steps.

Example 1

500 g diphenylmethane diisocyanate was heated to about 50° C. under the protection of $N_2$ while stirring, and a high-efficiency catalyst solution of 1-phenyl-3-methyl-3-phospholene (i.e., a solution of 1-phenyl-3-methyl-3-phospholene-1-oxide) with a catalyst amount of 0.5 ppm (0.025 g) was added, after mixing the mixture was quickly heated to 200° C., and after reacting for 90 minutes, 200 g diphenylmethane diisocyanate was further added, then 200 ppm (0.1 g) of terminator diphenyldifluorosilane and 50 ppm (0.025 g) of terminator p-toluenesulfonic anhydride were added, the temperature was rapidly cooled to 60° C., after stirring the mixture for 30 minutes, 200 g diphenylmethane diisocyanate was further added again, and the temperature was raised to 70-80° C., and stirred for 120 min to obtain the final product. The test results of the final product are shown in tables 1-2.

This example can also be performed according to the following steps:

500 g of diphenylmethane diisocyanate was heated to about 50° C. while stirring under the protection of $N_2$, and a high-efficiency catalyst solution of 1-phenyl-3-methyl-3-phospholene with a catalyst amount of 0.025 g was added, after mixing the mixture was quickly heated to 200° C., and after reacting for 90 minutes, 400 g diphenylmethane diisocyanate was further added, the temperature was rapidly cooled to 60° C., 0.1 g terminator diphenyldifluorosilane and 0.025 g terminator p-toluenesulfonic anhydride were added, and the mixture was stirred for 30 minutes and then heated to 70-80° C., and stirred for 120 minutes to obtain the final product. There is no significant change in the properties of this product relative to the properties of the product prepared according to the aforementioned steps.

Example 2

500 g diphenylmethane diisocyanate was heated to about 50° C. under the protection of $N_2$ while stirring, and a high-efficiency catalyst solution of 1-phenyl-3-methyl-3-phospholene (as a solution of 1-phenyl-3-methyl-3-phospholene-1-oxide) with a catalyst amount of 0.5 ppm (0.025 g) was added, after mixing the mixture was quickly heated to 200° C., and after reacting for 90 minutes, 200 g diphenylmethane diisocyanate was further added, then 200 ppm (0.1 g) of terminator diphenyldichlorosilane and 50 ppm (0.025 g) of terminator trifluoromethylsulfonic anhydride were added, the temperature was rapidly cooled to 60° C., after stirring the mixture for 30 minutes, then 200 g diphenylmethane diisocyanate was further added again, and the temperature was raised to 70-80° C., and stirred for 120 min to obtain the final product. The test results of the final product are shown in tables 1-2.

This example can also be performed according to the following steps:

500 g diphenylmethane diisocyanate was heated to about 50° C. while stirring under the protection of $N_2$, and a high-efficiency catalyst solution of 1-phenyl-3-methyl-3-phospholene with a catalyst amount of 0.025 g was added, after mixing the mixture was quickly heated to 200° C., and after reacting for 90 minutes, 400 g diphenylmethane diisocyanate was further added, the temperature was rapidly cooled to 60° C., 0.1 g terminator diphenyldichlorosilane and 0.025 g terminator trifluoromethylsulfonic anhydride were added, and the mixture was stirred for 30 minutes and then heated to 70-80° C., and stirred for 120 minutes to obtain the final product. There is no significant change in the properties of this product relative to the properties of the product prepared according to the aforementioned steps.

Example 3

500 g diphenylmethane diisocyanate was heated to about 50° C. under the protection of $N_2$ while stirring, and a high-efficiency catalyst solution of 1-methyl-3-methyl-3-phospholene-1-oxide (i.e., a solution of 1-methyl-3-methyl-3-phospholene-1-oxide) with a catalyst amount of 1 ppm (0.05 g) was added, after mixing the mixture was quickly heated to 120° C., and after reacting for 200 minutes, 200 g diphenylmethane diisocyanate was further added, then 200 ppm (0.1 g) of terminator tritylfluorosilane and 50 ppm (0.025 g) of terminator p-toluenesulfonic anhydride were added, the temperature was rapidly cooled to 60° C., after stirring the mixture for 30 minutes, then 200 g diphenylmethane diisocyanate was further added again, and the temperature was raised to 70-80° C., and stirred for 120 min to obtain the final product. The test results of the final product are shown in tables 1-2.

This example can also be performed according to the following steps: 500 g diphenylmethane diisocyanate was heated to about 50° C. under the protection of $N_2$ while stirring, and a high-efficiency catalyst solution of 1-phenyl-3-methyl-3-phospholene-1-oxide (i.e., a solution of 1-phenyl-3-methyl-3-phospholene-1-oxide) with a catalyst amount of 0.05 g was added, after mixing the mixture was quickly heated to 120° C., and after reacting for 200 minutes, 400 g diphenylmethane diisocyanate was further added, the temperature was rapidly cooled to 60° C., 0.1 g terminator tritylfluorosilane and 0.025 g terminator p-toluenesulfonic anhydride were added, after stirring the mixture for 30 minutes, the temperature was raised to 70-80° C., and stirred for 120 min to obtain the final product. There is no significant change in the properties of this product relative to the properties of the product prepared according to the aforementioned steps.

Example 4

500 g diphenylmethane diisocyanate was heated to about 50° C. under the protection of $N_2$ while stirring, and a high-efficiency catalyst solution of 1-methyl-3-methyl-3-phospholene-1-oxide (as a solution of 1-methyl-3-methyl-3-phospholene-1-oxide) with a catalyst amount of 0.5 ppm (0.025 g) was added, after mixing the mixture was quickly heated to 200° C., and after reacting for 90 minutes, 200 g diphenylmethane diisocyanate was further added, then 100 ppm (0.05 g) of terminator diphenyldifluorosilane and 20 ppm (0.01 g) of terminator trifluoromethylsulfonic anhydride were added, the temperature was rapidly cooled to 60° C., after stirring the mixture for 30 minutes, then 200 g diphenylmethane diisocyanate was further added again, then the temperature was raised to 70-80° C., and stirred for 120 min to obtain the final product. The test results of the final product are shown in tables 1-2.

This example can also be performed according to the following steps: 500 g diphenylmethane diisocyanate was heated to about 50° C. under the protection of $N_2$ while stirring, and a high-efficiency catalyst solution of 1-phenyl-3-methyl-3-phospholene-1-oxide (a solution of 1-phenyl-3-methyl-3-phospholene-1-oxide) with a catalyst amount of 0.025 g was added, after mixing the mixture was quickly heated to 200° C., and after reacting for 90 minutes, 400 g diphenylmethane diisocyanate was further added, the temperature was rapidly cooled to 60° C., 0.05 g terminator diphenyldifluorosilane and 0.01 g terminator trifluoromethylsulfonic anhydride were added, after stirring the mixture for 30 minutes, the temperature was raised to 70-80° C., and stirred for 120 min to obtain the final product. There is no significant change in the properties of this product relative to the properties of the product prepared according to the aforementioned steps.

Comparative Example 2

500 g diphenylmethane diisocyanate was heated to about 50° C. under the protection of $N_2$ while stirring, and a high-efficiency catalyst solution of 1-phenyl-3-methyl-3-pholene (i.e., a solution of 1-phenyl-3-methyl-3-phospholene-1-oxide) with a catalyst amount of 0.5 ppm (0.025 g) was added, after mixing the mixture was quickly heated to 200° C., and after reacting for 90 minutes, 200 g diphenylmethane diisocyanate was further added, then 10 ppm (0.025 g) of terminator trimethylsilyl trifluoromethanesulfonate was added, the temperature was rapidly cooled to 60° C., after stirring the mixture for 30 minutes, then 200 g diphenylmethane diisocyanate was further added again, then the temperature was raised to 70-80° C., and stirred for 120 min to obtain the final product. The test results of the final product are shown in tables 1-2.

This comparative example can also be performed according to the following steps: 500 g diphenylmethane diisocyanate was heated to about 50° C. while stirring under the protection of $N_2$, and a high-efficiency catalyst solution of 1-phenyl-3-methyl-3-phospholene with a catalyst amount of 0.025 g was added, after mixing the mixture was quickly heated to 200° C., and after reacting for 90 minutes, 400 g diphenylmethane diisocyanate was further added, the temperature was rapidly cooled to 60° C., 0.025 g of terminator trimethylsilyl trifluoromethanesulfonate was added, and the mixture was stirred for 30 minutes and then heated to 70-80° C., and stirred for 120 minutes to obtain the final product. There is no significant change in the properties of this product relative to the properties of the product prepared according to the aforementioned steps.

Comparative Example 3

500 g diphenylmethane diisocyanate was heated to about 50° C. under the protection of $N_2$ while stirring, and a high-efficiency catalyst solution of 1-phenyl-3-methyl-3-pholene (i.e., a solution of 1-phenyl-3-methyl-3-phospholene-1-oxide) with a catalyst amount of 0.5 ppm 0.025 g) was added, after mixing the mixture was quickly heated to 200° C., and after reacting for 90 minutes, 200 g diphenylmethane diisocyanate was further added, then 10 ppm (0.005 g) of terminator trimethylsilyl trifluoromethanesulfonate compounding with 200 ppm (0.1 g) of dibutyl phosphate was added, the temperature was rapidly cooled to 60° C., after stirring the mixture for 30 minutes, then 200 g diphenylmethane diisocyanate was further added again, then the temperature was raised to 70-80° C., and stirred for 120 min to obtain the final product. The test results of the final product are shown in tables 1-2.

This comparative example can also be performed according to the following steps: 500 g diphenylmethane diisocyanate was heated to about 50° C. while stirring under the protection of $N_2$, and a high-efficiency catalyst solution of 1-phenyl-3-methyl-3-phospholene with a catalyst amount of 0.025 g was added, after mixing the mixture was quickly heated to 200° C., and after reacting for 90 minutes, 400 g diphenylmethane diisocyanate was further added, the temperature was rapidly cooled to 60° C., 0.005 g terminator trimethylsilyl trifluoromethanesulfonate compounding with 0.1 g dibutyl phosphate was added, and the mixture was stirred for 30 minutes and then heated to 70-80° C., and stirred for 120 minutes to obtain the final product. There is no significant change in the properties of this product relative to the properties of the product prepared according to the aforementioned steps.

Comparative Example 4

500 g diphenylmethane diisocyanate was heated to about 50° C. under the protection of $N_2$ while stirring, and a high-efficiency catalyst solution of 1-phenyl-3-methyl-3-pholene (i.e., a solution of 1-phenyl-3-methyl-3-phospholene-1-oxide) with a catalyst amount of 0.5 ppm (0.025 g) was added, after mixing the mixture was quickly heated to 200° C., and after reacting for 90 minutes, 200 g diphenylmethane diisocyanate was further added, then 50 ppm (0.025 g) of terminator p-toluenesulfonic anhydride was added, the temperature was rapidly cooled to 60° C., after stirring the mixture for 30 minutes, 200 g diphenylmethane diisocyanate was further added again, then the temperature was raised to 70-80° C., and stirred for 120 min to obtain the final product. The test results of the final product are shown in tables 1-2.

This comparative example can also be performed according to the following steps: 500 g diphenylmethane diisocyanate was heated to about 50° C. while stirring under the protection of $N_2$, and a high-efficiency catalyst solution of 1-phenyl-3-methyl-3-phospholene with a catalyst amount of 0.025 g was added, after mixing the mixture was quickly heated to 200° C., and after reacting for 90 minutes, 400 g diphenylmethane diisocyanate was further added, the temperature was rapidly cooled to 60° C., 0.025 g terminator p-toluenesulfonic anhydride was added, and the mixture was stirred for 30 minutes and then heated to 70-80° C., and stirred for 120 minutes to obtain the final product. There is no significant change in the properties of this product relative to the properties of the product prepared according to the aforementioned steps.

Comparative Example 5

500 g diphenylmethane diisocyanate was heated to about 50° C. under the protection of $N_2$ while stirring, and a high-efficiency catalyst solution of 1-phenyl-3-methyl-3-pholene (i.e., a solution of 1-phenyl-3-methyl-3-phospholene-1-oxide) with a catalyst amount of 0.5 ppm (0.025 g) was added, after mixing the mixture was quickly heated to 200° C., and after reacting for 90 minutes, 200 g diphenylmethane diisocyanate was further added, then 50 ppm (0.025 g) of terminator methyl trifluoromethanesulfonate was added, the temperature was rapidly cooled to 60° C., after stirring the mixture for 30 minutes, 200 g diphenylmethane diisocyanate was further added again, then the temperature was raised to 70-80° C., and stirred for 120 min to obtain the final product. The test results of the final product are shown in tables 1-2.

This comparative example can also be performed according to the following steps: 500 g diphenylmethane diisocyanate was heated to about 50° C. while stirring under the protection of $N_2$, and a high-efficiency catalyst solution of 1-phenyl-3-methyl-3-phospholene with a catalyst amount of 0.025 g was added, after mixing the mixture was quickly heated to 200° C., and after reacting for 90 minutes, 400 g diphenylmethane diisocyanate was further added, the temperature was rapidly cooled to 60° C., 0.025 g terminator methyl trifluoromethanesulfonate was added, and the mixture was stirred for 30 minutes and then heated to 70-80° C., and stirred for 120 minutes to obtain the final product. There is no significant change in the properties of this product relative to the properties of the product prepared according to the aforementioned steps.

The comparison of each product in storage stability and color number is shown in tables 1-2.

Wherein, the viscosity refers to the national standard GB/T 12009.3-2009 of the People's Republic of China, polymethylene polyphenyl isocyanate, determination in the viscosity of the third part.

The determination of NCO refers to the national standard GB/T 12009.4-2016 of the People's Republic of China, aromatic isocyanates for the production of polyurethane, determination of the isocyanate content in the fourth part.

The color number is determined by a color number instrument, and the color number instrument model is BYK-LCSIII.

TABLE 1

Comparison table of each product in storage stability and color number

| | terminator | amount of the terminator PPM | initial viscosity of the product CP | viscosity stored at 30° C. (cp) 1 month | 2 months | 6 months | viscosity after 8 h degradation at high temperature (80° C.) (cp) |
|---|---|---|---|---|---|---|---|
| Comparative Example 1 | diphenyldifluorosilane | 200 | 42 | 43 | 46 | 53 | 90 |
| Example 1 | diphenyldifluorosilane/ p-toluenesulfonic anhydride | 200/50 | 40 | 41 | 42 | 44 | 45 |
| Example 2 | diphenyldichlorosilane/ trifluoromethanesulfonic anhydride | 200/50 | 41 | 43 | 44 | 47 | 46 |
| Example 3 | tritylfluorosilane/ p-toluenesulfonic anhydride | 200/50 | 41 | 43 | 45 | 48 | 48 |
| Example 4 | diphenyldifluorosilane/ trifluoromethanesulfonic anhydride | 100/20 | 42 | 43 | 47 | 49 | 48 |
| Comparative Example 2 | trimethylsilyl trifluoromethanesulfonate | 50 | 43 | 48 | 50 | 63 | 120 |
| Comparative Example 3 | trimethylsilyl trifluoromethanesulfonate/ dibutyl phosphate | 10/200 | 41 | 42 | 45 | 51 | 105 |
| Comparative Example 4 | p-toluenesulfonic anhydride | 50 | 43 | 52 | 73 | 112 | 180 |
| Comparative Example 5 | methyl trifluoromethanesulfonate | 50 | 41 | 57 | 83 | 140 | 230 |

TABLE 2

Comparison table of each product in storage stability and color number

| | terminator | initial NCO of the product % | NCO % stored at 30° C. 1 month | 2 months | 6 months | NCO % after 8 h degradation at high temperature (80° C.) | Hasson color number of the product (color number) initial | 2 months |
|---|---|---|---|---|---|---|---|---|
| Comparative Example 1 | diphenyldifluorosilane | 28.88 | 28.82 | 28.71 | 28.53 | 28.12 | 20 | 30 |
| Example 1 | diphenyldifluorosilane/ p-toluenesulfonic anhydride | 28.93 | 28.91 | 28.88 | 28.72 | 28.72 | 20 | 25 |
| Example 2 | diphenyldichlorosilane/ trifluoromethanesulfonic anhydride | 28.87 | 28.85 | 28.78 | 28.68 | 28.65 | 30 | 35 |
| Example 3 | tritylfluorosilane/ p-toluenesulfonic anhydride | 28.89 | 28.87 | 28.83 | 28.78 | 28.79 | 30 | 35 |
| Example 4 | diphenyldifluorosilane/ trifluoromethanesulfonic anhydride | 28.87 | 28.81 | 28.79 | 28.74 | 28.75 | 30 | 35 |
| Comparative Example 2 | trimethylsilyl trifluoromethanesulfonate | 28.85 | 28.72 | 28.53 | 28.31 | 27.53 | 150 | 180 |

TABLE 2-continued

Comparison table of each product in storage stability and color number

| | terminator | initial NCO of the product % | NCO % stored at 30° C. | | | NCO % after 8 h degradation at high temperature (80° C.) | Hasson color number of the product (color number) | |
|---|---|---|---|---|---|---|---|---|
| | | | 1 month | 2 months | 6 months | | initial | 2 months |
| Comparative Example 3 | trimethylsilyl trifluoromethanesulfonate/ dibutyl phosphate | 28.82 | 28.77 | 28.62 | 28.46 | 27.88 | 50 | 60 |
| Comparative Example 4 | p-toluenesulfonic anhydride | 28.91 | 28.21 | 28.03 | 27.24 | 26.56 | 40 | 70 |
| Comparative Example 5 | methyl trifluoromethanesulfonate | 28.91 | 28.61 | 28.28 | 27.14 | 26.35 | 140 | 150 |

Referring to Comparative Example 2, the modified isocyanate product has a high appearance color number and its high temperature stability is not ideal; the modified isocyanate products of Comparative Examples 3-5 have ideal storage stability at room temperature, but the stability is not ideal at high temperature, and NCO decreases significantly and viscosity increases greatly; it can be seen from Comparative Example 1 that by using of diphenyldifluorosilane alone, the stability at high temperature is poor; Examples 1-4 show that after compounding halosilane organic with p-toluenesulfonic anhydride, the stability is ideal at both room temperature and high temperature, and the color number is also lower than that in other examples.

The invention claimed is:

1. A preparation method of a light colored modified isocyanate mixture, the method includes the following steps:
   a) subjecting the isocyanate group of a raw material isocyanate to carbodiimidization under the action of a phosphorus heterocyclic catalyst to obtain a reaction solution of modified isocyanate containing carbodiimide and/or uretonimine derivatives;
   b) adding a compounded terminator to the reaction solution obtained in step a) to terminate the carbodiimidization;
   the compounded terminator is a compound of a halosilane organic and a sulfonic anhydride substance.

2. The preparation method according to claim 1, wherein, the reaction of step a) is carried out at a temperature of 40° C.-210° C.

3. The preparation method according to claim 1, wherein, the halosilane organic has a chemical formula of the following formula (I):

$$R_1X_3Si \text{ or } R_1R_2X_2Si \text{ or } R_1R_2R_3X_1Si \quad (I)$$

in the molecular formula (I), $R_1$, $R_2$ and $R_3$ independently represent aliphatic, aromatic, aralphatic, cycloaliphatic groups optionally containing heteroatoms, wherein $R_1$, $R_2$ and $R_3$ can be the same or different; and two groups of $R_1$, $R_2$ and $R_3$ can be connected to each other to form a ring structure;

X represents the halogen element selected from the group consisting of fluorine, chlorine, bromine and iodine.

4. The preparation method according to claim 1, wherein, the sulfonic anhydride substance has the following structural formula (II):

in the structural formula (II), $R_4$ and $R_5$ independently represent aliphatic, aromatic, aralphatic, or cycloaliphatic groups optionally contain heteroatoms and/or other functional groups, wherein $R_4$ and $R_5$ can be the same or different, the two groups $R_4$ and $R_5$ are optionally connected to each other to form a ring structure.

5. The preparation method according to claim 1, wherein, the compounded terminator is a compound of diphenyldifluorosilane and p-toluenesulfonic anhydride.

6. The preparation method according to claim 1, wherein, the temperature condition of adding the compounded terminator to terminate the carbodiimidation of step b) is 40-70° C.

7. The preparation method according to claim 1, wherein, the amount of compounded terminator is based on the weight of the raw material isocyanate, the amount of halosilane organic is 50-2000 ppm; the amount of sulfonic anhydride substance is 10-200 ppm.

8. The preparation method according to claim 1, wherein, the catalyst used for preparing the isocyanate containing carbodiimide and/or uretonimine derivatives is a phospholene catalyst and/or a phospholene oxide, the amount of the catalyst is 0.1-10 ppm, relative to the weight of the raw material isocyanate.

9. The preparation method according to claim 1, wherein, the raw material isocyanate is one or more selected from the group consisting of aromatic, aralphatic, aliphatic, and cycloaliphatic diisocyanates.

10. The preparation method according to claim 1, wherein, when the reaction time of the carbodiimidation reaches 10 min-24 h, the compounded terminator is added to terminate the reaction.

11. The preparation method according to claim 3, wherein, in the molecular formula (I), $R_1$, $R_2$ and $R_3$ independently represent C1-C10 hydrocarbyl, C6-C15 aromatic, C7-C15 aralphatic, or C3-C12 cycloaliphatic groups optionally containing heteroatoms.

12. The preparation method according to claim 11, wherein in the molecular formula (I), $R_1$, $R_2$ and $R_3$ independently represent phenyl, tolyl, ethylphenyl, phenmethyl or phenyethyl optionally containing heteroatoms.

13. The preparation method according to claim 3, wherein, the halosilane organic is selected from the group consisting of diphenyldifluorosilane, diphenyldichlorosilane, tritylfluorosilane, tert-butyltrichlorosilane and combinations thereof.

14. The preparation method according to claim 4, wherein, in the structural formula (II), $R_4$ and $R_5$ independently represent C1-C10 hydrocarbyl, C6-C15 aromatic, C7-C15 araliphatic, or C3-C12 cycloaliphatic groups optionally contain heteroatoms and/or other functional groups.

15. The preparation method according to claim 14, wherein, in the structural formula (II), $R_4$ and $R_5$ independently represent phenyl, tolyl, ethylphenyl, phenmethyl, phenethyl, cyclopropyl, cyclobutyl, cyclohexyl or cyclopentyl optionally containing heteroatoms and/or other functional groups.

16. The preparation method according to claim 4, wherein, the sulfonic anhydride substance is selected from the group consisting of p-toluenesulfonic anhydride, methanesulfonic anhydride, ethylsulfonic anhydride, trifluoromethanesulfonic anhydride and combinations thereof.

17. The preparation method according to claim 7, wherein, the amount of compounded terminator is based on the weight of the raw material isocyanate, the amount of halosilane organic is 100-600 ppm; the amount of sulfonic anhydride substance is 10-100 ppm.

18. The preparation method according to claim 7, wherein, the compounding mass ratio of the halosilane organic and the sulfonic anhydride substance is 2-6:1.

19. The preparation method according to claim 8, wherein, the amount of the catalyst is 0.2-2 ppm relative to the weight of the raw material isocyanate.

20. The preparation method according to claim 9, wherein, the raw material isocyanate is diphenylmethane diisocyanate.

* * * * *